United States Patent
Choe et al.

(10) Patent No.: US 11,077,151 B2
(45) Date of Patent: Aug. 3, 2021

(54) ASCAROSIDE TREATMENT OF AUTOIMMUNE AND INFLAMMATORY DISEASES

(71) Applicants: California Institute of Technology, Pasadena, CA (US); Boyce Thompson Institute for Plant Research, Ithaca, NY (US)

(72) Inventors: Andrea Choe, Pasadena, CA (US); Paul W. Sternberg, San Marino, CA (US); Frank C. Schroeder, Ithaca, NY (US)

(73) Assignees: California Institute of Technology, Pasadena, CA (US); Boyce Thompson Institute for Plant Research, Ithaca, NY (US)

( * ) Notice: Subject to any disclaimer, the term of this patent is extended or adjusted under 35 U.S.C. 154(b) by 126 days.

(21) Appl. No.: 16/327,659

(22) PCT Filed: Aug. 25, 2017

(86) PCT No.: PCT/US2017/048665
§ 371 (c)(1),
(2) Date: Feb. 22, 2019

(87) PCT Pub. No.: WO2018/039591
PCT Pub. Date: Mar. 1, 2018

(65) Prior Publication Data
US 2019/0175663 A1    Jun. 13, 2019

Related U.S. Application Data

(60) Provisional application No. 62/379,651, filed on Aug. 25, 2016.

(51) Int. Cl.
| | |
|---|---|
| *A61K 35/62* | (2006.01) |
| *A61P 1/04* | (2006.01) |
| *A61K 31/4178* | (2006.01) |
| *A61K 31/7028* | (2006.01) |
| *A61K 45/06* | (2006.01) |
| *A61P 37/06* | (2006.01) |
| *A61P 3/10* | (2006.01) |
| *A61K 31/573* | (2006.01) |
| *G01N 33/68* | (2006.01) |
| *A61K 31/4439* | (2006.01) |
| *A61K 31/56* | (2006.01) |
| *A61K 31/7042* | (2006.01) |
| *A61K 47/26* | (2006.01) |

(52) U.S. Cl.
CPC .......... *A61K 35/62* (2013.01); *A61K 31/4178* (2013.01); *A61K 31/4439* (2013.01); *A61K 31/56* (2013.01); *A61K 31/573* (2013.01); *A61K 31/7028* (2013.01); *A61K 31/7042* (2013.01); *A61K 45/06* (2013.01); *A61K 47/26* (2013.01); *A61P 1/04* (2018.01); *A61P 3/10* (2018.01); *A61P 37/06* (2018.01); *G01N 33/6869* (2013.01); *Y02A 50/30* (2018.01)

(58) Field of Classification Search
CPC combination set(s) only.
See application file for complete search history.

(56) References Cited

U.S. PATENT DOCUMENTS

| | | | |
|---|---|---|---|
| 5,945,445 | A | 8/1999 | Barringer et al. |
| 6,444,686 | B1 | 9/2002 | Ko et al. |
| 8,318,146 | B1 | 11/2012 | Teal et al. |
| 9,445,596 | B2 | 9/2016 | Schroeder et al. |
| 9,487,551 | B2 | 11/2016 | Choe et al. |
| 9,534,008 | B2 | 1/2017 | Choe et al. |
| 9,868,754 | B2 | 1/2018 | Choe et al. |
| 1,018,396 | A1 | 1/2019 | Choe et al. |
| 10,479,813 | B2 | 11/2019 | Choe et al. |
| 2005/0075389 | A1 | 4/2005 | Paik et al. |
| 2008/0188646 | A1 | 8/2008 | Jung et al. |
| 2009/0264392 | A1 | 10/2009 | Warndahl et al. |
| 2010/0048497 | A1 | 2/2010 | Andersch et al. |
| 2010/0056469 | A1 | 3/2010 | Langewald et al. |
| 2014/0364586 | A1 | 12/2014 | Watts et al. |
| 2020/0262856 | A1 | 8/2020 | Choe et al. |

FOREIGN PATENT DOCUMENTS

| | | |
|---|---|---|
| DE | 10163602 A1 | 7/2003 |
| KR | 10-2009-0088496 | 8/2009 |
| WO | WO-96/19920 | 7/1996 |
| WO | WO-2005/110040 A2 | 11/2005 |
| WO | WO-2009/102736 | 8/2009 |
| WO | WO-2013/022985 A2 | 2/2013 |
| WO | WO-2013/022996 A2 | 2/2013 |
| WO | WO-2013/022997 A2 | 2/2013 |
| WO | WO-2013/023000 A2 | 2/2013 |
| WO | WO-2013/039872 A1 | 3/2013 |
| WO | WO-2014/145380 A2 | 9/2014 |
| WO | WO-2014/151648 A1 | 9/2014 |
| WO | WO-2018/039593 A1 | 3/2018 |

OTHER PUBLICATIONS

European C. elegans Neurobiology Meeting; Oct. 9, 2010. (http://ww.worms.gr/ewnm2010/files/abstracts.pdf).
Ben-Yakir, D. et al., "Evaluation of entomopathogenic nematodes for biocontrol of the European Corn Borer, *Ostrinia nubilalis*, on sweet corn in Israel," Phytoparasitica, 26(2):101-8 (1998).
Bose et al., "Complex small-molecule architectures regulate phenotypic plasticity in a nematode," Angew Chem Int Ed, 51:12438-43 (2012).
Butcher et al., "An Indole-Containing Dauer Pheromone Component with Unusual Dauer Inhibitory Activity at Higher Concentrations," Organic Letters 11(14):3100-3103 (2009).
Butcher et al., "Biosynthesis of the *Caenorhabditis elegans* dauer pheromone," PNAS, 106(6):1875-1879 (2009).
Butcher, R. A. "Small-molecule pheromonese that control dauer development in *Caenorhadbiditus elegans*," J. Nat. Chem. Ciol. 3(7): 420-422 (2007).

(Continued)

*Primary Examiner* — Heidi Reese
(74) *Attorney, Agent, or Firm* — Foley Hoag LLP (57) ABSTRACT

The present invention relates to the use of ascr #7 for preventing or treating IL-6 and/or IL-1β-mediated diseases.

18 Claims, 7 Drawing Sheets

(56) References Cited

OTHER PUBLICATIONS

Cheng et al., "Insertational mutagenesis of a fungal biocontrol agent led to discovery of a rare cellobiose lipid with antifungal activity," Appl Environ Microb, 69(5):2595-602 (2003).

Choe et al., "Ascaroside Signaling is Widely Conserved Among Nematodes," Curr Biol., 22(9):772-780 (2012).

Choe. "Pheromones in Free-Living and Parasitic Nematodes," Thesis for California Institute of Technology, (Jun. 17, 2011) (Made publically available Dec. 2, 2013).

Chuman et al., "Identification and Characterization of Nematode Pheromones," National High Magnetic Field Laboratory (2009).

European Extended Search Report for EP Patent Application: 12822518.2 dated Jan. 30, 2015.

European Extended Search Report for EP Patent Application: 12822698.2 dated Mar. 4, 2015.

European Search Report for EP Patent Application No. 12822518.2 dated Feb. 17, 2017.

Gallo et al., "Effects of a Caenorhabditis elegans dauer pheromone ascaroside on physiology and signal transduction pathways," J. Chem. Ecol., 35(2):272-279 (2009).

International Search Report and Written Opinion for International Application No. PCT/US2017/048665 dated Dec. 20, 2017.

International Search Report and Written Opinion for International Application No. PCT/US2017/048672 dated Dec. 18, 2017.

International Search Report dated Jul. 25, 2013 from PCT/US2012/050016.

International Search Report dated May 2, 2013 from PCT/US2012/050032.

Jeong et al., "Chemical structure and biological activity of the Caenorhabditis elegans dauer-inducing pheromone," Nature, 433(7025):541-545 (2005).

Kaplan et al., "Ascaroside Expression in *Caenorhabditis elegans* Is Strongly Dependent on Diet and Developmental Stage," PLOSOne, 6(3):e17804 (2011).

Lacey, L.A. et al., "Insect pathogens as biological control agents: Do they have a future?" Biol Control, 21:230-48 (2001).

Martin et al., "Improved Synthesis of an Ascaroside Pheromone Controlling Dauer Larva Development in Caenorhabditis Elegans," Synthesis, 20:3488 (2009).

Noh et al., "Quantitative determination of daumone in rat plasma by liquid chromatography-mass spectrometry," J. Pharm. Biomed. Anal., 56(1):114-117 (2011).

Pungaliya et al., "A shortcut to identifying small molecule signals that regulate behavior and development in Caenorgabditis elegans," PNAS, 106(19): 7708-7713 (2009).

Riga, E. et al., "In vitro effect of marigold seed exudates on plant parasitic nematodes," Phytoprotection, 86:31-5 (2004).

Srinivasan et al., "A blend of small molecules regulates both mating and development in *Caenorhabditis elegans*," Nat Lett, 454:1115-9 (2008)/.

Von Reuss et al., "Comparative Metabolomics Reveals Biogenesis of Ascarosides, a Modular Library of Small-Molecule Signals in C. elegans," Journal of the American Chemical Society, 134(3):1817-1824 (2012).

Written Opinion for International Application No. PCT/US2012/050031 dated Feb. 13, 2013.

Written Opinion for International Application No. PCT/US2012/050037 dated Feb. 7, 2013.

U.S. Appl. No. 14/237,774, Granted.
U.S. Appl. No. 15/268,247, Abandoned.
U.S. Appl. No. 14/237,786, Granted.
U.S. Appl. No. 15/395,459, Abandoned.
U.S. Appl. No. 14/237,795, Granted.
U.S. Appl. No. 15/833,474, Granted.
U.S. Appl. No. 16/251,750, Granted.
U.S. Appl. No. 16/685,375, Pending.
U.S. Appl. No. 14/237,800, Granted.
U.S. Appl. No. 15/343,775, Abandoned.
U.S. Appl. No. 16/327,670, Pending.

International Search Report and Written Opinion for International Application No. PCT/US2020/033205 dated Aug. 27, 2020.

Extended European Search Report for EP Application No. 17844508.6 dated Feb. 20, 2020.

Extended European Search Report for EP Application No. EP 17844507 dated Feb. 20, 2020.

Extended European Search Report for EP Application No. EP 19169996 dated Jul. 26, 2019.

Manosalva et al., "Conserved nematode signalling molecules elicit plant defenses and pathogen resistance," Nature Communications, 6:7795 (2015).

Wisnewski et al., "Characterization of novel fucosyl- and tyvelosyl-containing glycoconjugates from Trichinella spiralis muscle stage larvae," Molecular and Biochemical Parasitology, 61(1):25-36 (1993).

ASCAROSIDE TREATMENT OF AUTOIMMUNE AND INFLAMMATORY DISEASES

RELATED APPLICATIONS

This application is a national-stage filing under 35 U.S.C. § 371 of International Application No. PCT/US2017/048665, filed Aug. 25, 2017, which claims the benefit of and priority to U.S. Provisional Patent Application Ser. No. 62/379,651, filed Aug. 25, 2016, each of which is hereby incorporated by reference in its entirety.

BACKGROUND

Many nematode species are known to parasitize humans, a relationship that is thought to have existed for thousands of years.

It has long been known that there is an inverse relationship between areas endemic with parasitic nematodes and areas with a high incidence of autoimmune disease. This observation spurred the hypothesis that parasitic nematodes may protect against autoimmune disease, and it has been corroborated by numerous human clinical trials and animal model studies, where ingestion of parasitic nematodes has alleviated disease symptoms.

Some nematode-based approaches for treating autoimmune and inflammatory diseases have been identified. A need exists for additional disease treatments for which factors and/or isolates of parasitic nematodes may offer possibilities.

SUMMARY

The present invention is based, at least in part, on the discovery that ascarosides, a family of small-molecule nematode pheromones, modulate the immune response and have a therapeutic effect on various autoimmune and inflammatory disorders. One of the ascarosides, ascr #7, markedly inhibits the hallmark pathologies in mouse models of asthma, inflammatory bowel disease, and type 1 diabetes, and significantly reduces both IL-6 and IL-1β secretion. These findings suggest that ascr #7 has a therapeutic effect in diseases where elevated levels of IL-6 and/or IL-1β contribute to the diseases' pathogeneses.

In some aspects, the invention provides a method of preventing, alleviating, or treating an IL-6- and/or IL-1β-mediated disease in a subject. The method comprises administering to the subject a composition comprising ascr #7 or a pharmaceutically acceptable salt or prodrug thereof.

Numerous embodiments are described that can be applied to any aspect of the present invention and/or combined with any other embodiment described herein. For example, in some embodiments, the subject has an elevated level of IL-6 and/or IL-1β. In some other embodiments, IL-6 and/or IL-1β contribute to one or more symptoms of the disease. In such embodiments, the method may comprise assessing the level of IL-6 and/or IL-1β in an affected tissue of the subject and, if the level exceeds 200% of a normal level for the affected tissue, administering ascr #7 or a pharmaceutically acceptable salt or prodrug thereof.

In some embodiments, the disease is Agammaglobulinemia, Amyloidosis, Ankylosing spondylitis, Anti-GBM/Anti-TBM nephritis, Antiphospholipid syndrome, Autoimmune hepatitis, Autoimmune inner ear disease, Atopic dermatitis, Asthma, Castleman disease, Celiac disease, Chagas disease, Chronic recurrent multifocal osteomyelitis, Cogan's syndrome, Cold agglutinin disease, CREST syndrome, Crohn's disease, Dermatomyositis, Devic's disease (neuromyelitis optica), Discoid lupus, Endometriosis, Eosinophilic esophagitis, Eosinophilic fasciitis, Evan's syndrome, Fibromyalgia, Giant cell arteritis, Giant cell myocarditis, Glomerulonephritis, Goodpasture's syndrome, Granulomatosis with polyangiitis, Graves' disease, Guillain-Barre syndrome, Hashimoto's thyroiditis, Hemolytic anemia, Henoch-Schonlein purpura, Hypogammaglobulinemia, Hypoproliferative anemia, IgA Nephropathy, Inclusion body myositis, Interstitial cystitis, Inflammatory Bowel Disease, Juvenile arthritis, Juvenile/Type 1 Diabetes, Juvenile myositis, Kawasaki syndrome, Lichen planus, Lichen sclerosus, Lupus (SLE), Meniere's disease, Multiple sclerosis, Myasthenia gravis, Microscopic polyangiitis, Optic neuritis, Pemphigus, Polyarteritis nodosa, Polymyalgia rheumatica, Polymyositis, Primary biliary cirrhosis, Primary sclerosing cholangitis, Psoriasis, Psoriatic arthritis, Rheumatic fever, Rheumatoid arthritis, Sarcoidosis, Sjogren's syndrome, Temporal arteritis/Giant cell arteritis, Transverse myelitis, Ulcerative colitis, Uveitis, Vasculitis, Vitiligo, Viral myocarditis, or Wegener's granulomatosis (Granulomatosis with Polyangiitis (GPA)).

In certain preferred embodiments, the disease is asthma, inflammatory bowel disease, or type 1 diabetes. In some preferred embodiments, the disease is eosinophilic esophagitis (EoE), while in other embodiments the disease is not EoE.

In some embodiments, the method further comprises administering an agent with an anti-inflammatory effect, such as a corticosteroid.

In some embodiments, the method further comprises administering a corticosteroid to the subject. In some embodiments, the corticosteroid is selected from aldosterone, betamethasone, budesonide, corticosterone, cortisol, cortisone, dexamethasone, fluticasone (e.g., fluticasone propionate), hydrocortisone, methylprednisolone, prednisolone, and prednisone. In some embodiments, the subject is a mammal. In certain embodiments, the mammal is a mouse or a human. In certain preferred embodiments, the mammal is a human.

In some aspects, the invention provides a method of reducing IL-6 and/or IL-1β production from a cell, comprising contacting the cell with a composition comprising ascr #7 or a pharmaceutically acceptable salt or prodrug thereof.

BRIEF DESCRIPTION OF THE DRAWINGS

FIG. 3B shows that ascr #7 diminishes resistance to air flow in a mouse model of asthma.

DETAILED DESCRIPTION

It has been determined herein that ascr #7 has a therapeutic effect in autoimmune and/or inflammatory diseases, e.g., where elevated levels of IL-6 and/or IL-1β contribute to the diseases' pathogeneses. Accordingly, the present invention relates, in part, to methods of alleviating, treating, or preventing an IL-6- and/or IL-1β-mediated disease in a subject by administering to the subject a composition comprising ascr #7 or a pharmaceutically acceptable salt or prodrug thereof. In other aspects, the present invention relates to methods of reducing IL-6 and/or IL-1β production from a cell by contacting the cell, or affiliated cells, with a composition comprising ascr #7 or a pharmaceutically acceptable salt or prodrug thereof.

I. Definitions

For convenience, certain terms employed in the specification, and appended claims are collected here.

The term "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "subject" refer to either a human or a non-human animal. This term includes mammals such as humans, primates, livestock animals (e.g., bovines, porcines), companion animals (e.g., canines, felines) and rodents (e.g., mice, rabbits and rats).

"About" and "approximately" shall generally mean an acceptable degree of error for the quantity measured given the nature or precision of the measurements. Typically, exemplary degrees of error are within 20%, preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "prodrug" is intended to encompass compounds which, under physiologic conditions, are converted into the therapeutically active agents of the present invention (e.g., ascr #7). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of the present invention (e.g., ascr #7) in a formulation represented above can be replaced with the corresponding suitable prodrug, e.g., wherein a hydroxyl in the parent compound is presented as an ester or a carbonate or carboxylic acid present in the parent compound is presented as an ester.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, alleviate, ameliorate, or stabilize the existing unwanted condition or side effects thereof).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Unless otherwise defined herein, scientific and technical terms used in this application shall have the meanings that are commonly understood by those of ordinary skill in the art. Generally, nomenclature and techniques relating to chemistry, molecular biology, cell and cancer biology, immunology, microbiology, pharmacology, and protein and nucleic acid chemistry, described herein, are those well-known and commonly used in the art.

II. Compositions

Ascr #7

Ascr #7 is an ascaroside produced by a nematode, e.g., *Nippostrongylus brasiliensis*.

Ascr #7 has the structure:

The compositions and methods disclosed herein may use any suitable form, prodrug, and/or salt of ascr #7 that exhibits the desired therapeutic effects in subjects.

Pharmaceutical Compositions

In certain embodiments, the present invention provides pharmaceutical compositions comprising ascr #7 or a pharmaceutically acceptable salt or prodrug thereof and a pharmaceutically acceptable carrier.

The compositions and methods of the present invention may be utilized to treat a subject in need thereof. In certain embodiments, the subject is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The subject receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. Pharmaceutically acceptable salt forms can include forms wherein the ratio of molecules comprising the salt is not 1:1. For example, the salt may comprise more than one ascr #7 molecule per molecule of base, such as two ascr #7 molecules per molecule of compound of base. As another example, the salt may comprise less than one ascr #7 molecule per molecule of base, such as two molecules of ascr #7 per molecule of lysine, or per atom of magnesium or zinc.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

III. Indications

In certain aspects, the invention provides methods of preventing, alleviating, or treating an autoimmune and/or inflammatory disease, e.g., an IL-6- and/or IL-1β-mediated disease, in a subject, comprising administering to the subject a composition comprising ascr #7 or a pharmaceutically acceptable salt and/or prodrug thereof.

In certain aspects, the invention provides use of ascr #7 in the manufacture of a medicament for the treatment of an autoimmune and/or inflammatory disease, e.g., an IL-6- and/or IL-1β-mediated disease.

Elevated levels of IL-6 and/or IL-1β have been found in patients with various diseases, and studies have shown that IL-6 and/or IL-1β contribute to these diseases' pathogeneses. These IL-6- and/or IL-1β-mediated diseases may include diseases that affect musculoskeletal or connective tissues. For example, IL-1RA, IL-6, and IL-8 have been found to be increased in patients with fibromyalgia (Rodriguez-Pinto et al. Immunology Letters 2014; 161:200-203). Elevated IL-6 and other inflammation markers have been found in patients with chronic nonbacterial osteomyelitis and chronic recurrent multifocal osteomyelitis in the absence of high-titer auto-antibodies (Hedrich et al. Pediatric Rheumatology 2013; 11:47). Analysis of serum from patients with juvenile dermatomyositis also showed significantly higher levels of MCP-1 and IL-6, than samples taken from healthy controls (Nistala et al. Arthritis Research & Therapy 2013; 15:R131). IL-6 was significantly elevated in patients with ankylosing spondylitis compared to the controls, and serum leptin and IL-6 levels correlated significantly with Bath Ankylosing Spondylitis Disease Activity Index (Elolemy et al. The Egyptian Rheumatologist 2013; 35:65-70). In addition, IL-6 is likely responsible in part for Th17 activity in cutaneous lupus erythematosus (Achtman and Werth, Arthritis Research & Therapy 2015; 17:182). IL-6 has a significant role in the pathophysiology of active systemic lupus erythematosus (SLE), and there is a good correlation between IL-6 and SLE disease activity (Umare et al. J Postgrad Med. 2017; 63(2):92-95). Expression of IL-1RI, and IL-1RII and their ligands, i.e., IL-1a and IL-1β was significantly higher in patients with polymyositis and dermatomyositis than in controls, which supports the hypothesis of a crucial role of IL-1 in the pathogenesis of polymyositis and dermatomyositis (Grundtman et al. ARTHRITIS & RHEUMATISM 2007; 56(2):674-687).

The IL-6- and/or IL-1β-mediated diseases may include diseases that affect renal system. For example, elevations of IL-1 and IL-6 were identified within 3 days of onset of anti-GBM glomerulonephritis (Kim et al. Kidney International 2004; 66:1826-1837). Another study shows that IL-6 plays an important role in the development glomerulonephritis with multinucleated giant cells, and regression of clinical symptoms was well correlated with a reduction in serum IL-6 levels (Ito et al. Am J Kidney Dis. 1995; 26(1):72-9). IL-6 and histamine were significantly greater in patients with interstitial cystitis than in the control (Lamale et al. Adult Urology 2006; 68(4)42-46). Higher production of IL-6, IL-8, monocyte chemotactic protein 1, TGF-β and fibronectin was found in patients with IgA nephropathy compared to that in healthy volunteers (Liang et al. Cell Physiol Biochem 2015; 36:1793-1808).

The IL-6- and/or IL-1β-mediated diseases may be dermatological disorders. For example, serum levels of both IL-6 and GM-CSF of the patients with both focal and generalized type of vitiligo were significantly higher than those of controls, while the serum level of IL-1β of patients with generalized type of vitiligo were significantly higher than those of controls and with segmental type of vitiligo. In addition, IL-6 level of the generalized type in progressive stage were significantly higher than those in stable states. These findings suggest that IL-6 and GM-CSF may be involved in the autoimmune mechanism of non-segmental vitiligo (Tu et al. Journal of Dermatological Science 2003; 31:73-78).

The IL-6- and/or IL-1β-mediated diseases may include diseases that affect reproductive system. For example, IL-6 was significantly higher in the serum of subjects with endometriosis than in the control group. Therefore, serum IL-6 provides a promising marker for nonsurgical prediction of endometriosis (Othman et al. European Journal of Obstetrics & Gynecology and Reproductive Biology 2008; 137: 240-246).

The IL-6- and/or IL-1β-mediated diseases may include diseases that affect cardiovascular system. For example, in both giant cell myocarditis and coxsackie virus induced viral myocarditis, levels of IL-1β and IL-6 in the pericardial effusion were elevated compared with the serum cytokines at the peak of inflammation (Nakayama et al. Jpn Circ J. 2000; 64(12):977-81). Increased levels of the Th17 enhancing cytokines, TGFβ, IL-6, and IL-23 can be found in the sera of patients with granulomatosis with polyangiitis (Wilde et al. Arthritis Research & Therapy 2012; 14: R227). The concentration of serum IL-6 was also significantly increased in patients with Henoch-Schonlein Purpura compared to controls (Su et al. International Immunopharmacology 2016; 39:246-250). Patients with Wegener's granulomatosis had elevated levels of IL-6 as well (Kobold et al. Ann Rheum Dis 1999; 58:237-245). In addition, serum IL-6 was elevated in patients with Giant Cell Arteritis and Polymyalgia Rheumatica, and IL-6 had the strongest association with disease activity compared to other cytokines measured in the serum (Van der Geest et al. Rheumatology 2015; 54:1397-1402). IL-6 showed significant correlations with the C-reactive protein (CRP) and erythrocyte sedimentation rates in 17 children with active rheumatic fever, and significant correlation was found between IL-6 levels and the white blood cell (WBC) counts (Yegin et al. Eur J Pediatr. 1997; 156(1):25-9). IL-6 was elevated in patients with Kawasaki Disease, and IL-6 is a critical cytokine in the Kawasaki Disease pathogenesis of autoimmune vasculitis (Tan et al. Indian Pediatrics 2013; 50:501-503).

The IL-6- and/or IL-1β-mediated diseases may include diseases that affect respiratory system. For example, IL-6 levels were specifically elevated in asthmatic subjects compared with healthy controls, and the relationship between asthma and lung function could be mediated by IL-6 (Neveu et al. Respiratory Research 2010; 11:28).

The IL-6- and/or IL-1β-mediated diseases may include diseases that affect hematological system. For example, circulating IL-6 may persist elevated in patients with giant cell arteritis and remain higher in patients who have experienced relapse (Garcia-Martinez et al. Arthritis Care & Research 2010; 62(6):835-841). Serum Th2 cytokine levels such as IL-6 and IL-1β were high and Th1 cytokines such as IL2 and IFN-γ were low at onset in a 1-year-old girl with Evans syndrome coexisting with histologically confirmed Langerhans cell histiocytosis (Tsuji et al. Int J Hematol 2008; 87:75-77). IVIG infusion significantly increased serum concentration of IL-6 in patients with primary hypogammaglobulinemia (Ibáñez et al. Biodrugs 2005; 19(1):59-65). Patients with Primary Anti-Phospholipid Syndrome had higher levels of IL-6 compared to controls, and IL-6 is known to induce the maturation of B-cells into plasma cells, which then secrete antibodies and contribute to the disease progress (Soltesz et al. Rheumatology 2008; 47: 1628-1634). IL-6 is elevated in patients with Chronic Cold Agglutinin Disease, and IL-6 plays a role in fever induction, which is thought to lead to blood hemolysis (Ulvestad et al. Scand. J. Immunol. 2001; 54:239-242). In addition, cytokine production by salivary gland epithelial cells from Sjögren's syndrome (SS) patients showed increased IL-6 and decreased TGFβ secretion. This imbalance may be critical in the regulation of Treg/Th17 cells and may foster a pathogenic milieu that may be causative and predictive in SS (Kawanami et al. PLOS ONE 2012; 7(10):101-106).

The IL-6- and/or IL-1β-mediated diseases may include diseases that affect gastrointestinal system. For example, the levels of pro-inflammatory cytokines, IL-2, IL-4, IL-6, IL-12p70, and IFNγ were increased 6-9-fold in the blood serum of patients with IBDs compared to that from controls (Toptygina et al. Biokhimiya, 2014; 79(12):1673-1679). IL-6 level was significantly elevated (281.5 pg/ml in the new/active EoE patient group compared to 16.2 pg/ml in the control group) in biopsy culture supernatant from esophageal samples from patients with eosinophilic esophagitis (Sayej et al. Clinical & Translational Immunology 2016; 5:25-36). The average serum IL-6 level in the EoE patients is also at least two-fold higher than the level in the healthy controls (Blanchard et al. J Allergy Clin Immunol. 2011; 127(1):208-17). In addition, the IL-1β gene was also significantly elevated (about 7-fold using microarray analysis and about 5.5-fold using real-time PCR) in biopsies from esophageal samples from patients with eosinophilic esophagitis (Blanchard et al. J Allergy Clin Immunol. 2011; 127(1):208-17). There was also a significant increase in median IL-6 staining in both the lamina propria and the epithelium of untreated celiac disease patients, when compared with treated celiac disease patients (Przemioslo et al. Gut 1994; 35:1398-1403). In addition, Type I diabetic children living in moderate altitude or at sea level showed elevated levels of IL-6, along with other pro-inflammatory cytokines (Allam et al. High Altitude Medicine & Biology 2014; 15(3):59-66). Patients with type 1 diabetes had higher levels of mannose binding lectin (MBL) compared to siblings of these patients, and increased MBL levels positively correlated with IL-1β, IL-12, and IL-18 (Sildorf et al. Molecular Immunology 2014; 62:71-76). The hepatic expression of IL-17, IL-23, IL-6, and IL-1β, etc. in patients with autoimmune hepatitis were also significantly increased and were associated with increased inflammation and fibrosis (Zhao et al. PLOS ONE 2011; 6(4):124-131). Muramyl dipeptides, the minimal NOD2/CARD15 (mutations in which increases the susceptibility for Crohn's disease) activating component of peptidoglycan induced IL-1β and IL-8 transcripts (Li et al. Human Molecular Genetics, 2004; 13(16):1715-1725).

The IL-6- and/or IL-1β-mediated diseases may include diseases that physically affect the nervous system. For example, levels of IL-6 among the transverse myelitis patient population directly correlated with markers of tissue injury and the severity of paralysis (Kaplin et al. J Clin Invest. 2005; 115(10):2731-41). IL-2 and IL-6 were also increased in patients with Guillain-Barré syndrome (Creange et al. J Neurol Neurosurg Psychiatry 1998; 64:162-165). In addition an IL-6 receptor antibody has been found to treat AA amyloidosis (Ando, Rinsho Shinkeigaku (Cln Neurol) 2015; 55:797-803).

In addition, steroid-resistant patients with autoimmune inner ear disease have increased expression of IL-1β (Rauch S D, J Clin Invest. 2014; 124(9):3685-3687).

The IL-6- and/or IL-1β-mediated diseases may include diseases that affect endocrine system. For example, IL-6 was elevated in patient group with Graves' disease (Niyazoglu et al. Gene 547 (2014) 226-232). Levels of IL-6 was also significantly increased in Hashimoto thyroiditis patients compared to the control group, and higher IL-6 levels are associated with increased risk factor in Hashimoto thyroiditis (Koc et al. Immunobiology 2014; 219:531-536). IL-6 was markedly increased in Graves' disease patients compared to normal controls (Al-Humaidi M A, Saudi Medical Journal 2000; 21(7):639-644).

The IL-6- and/or IL-1β-mediated diseases may include diseases that affect multiple tissues or organs systematically. For example, IL-6 is associated with diabetes, Crohn's disease, and rheumatoid arthritis (Maggio et al. J Gerontol A Biol Sci Med Sci. 2006; 61(6): 575-584).

As IL-6 and/or IL-1β plays an important role in many autoimmune and inflammatory diseases, targeting IL-6 and/or IL-1β is being used as a therapy for these diseases. For example, IL6 receptor antibody has been found to be effective in treating Amyloid A (AA) amyloidosis (Ando Y., Rinsho Shinkeigaku. 2015; 55(11):797-803). With the treatment of humanized anti-IL-6 receptor antibody, the serum hemoglobin level of patients with autoimmune hemolytic anemia gradually increased and normalized within 4 months (Kunitomi et al. Int J Hematol. 2004; 80:246-249).

Tocilizumab, a humanized anti-IL-6 receptor antibody, has been approved as a biological drug for the treatment of rheumatoid arthritis, Castleman's disease and systemic juvenile idiopathic arthritis, and is expected to be applicable to various other autoimmune and chronic inflammatory diseases (Tanaka et al. Int J Biol Sci 2012; 8(9):1227-1236). Other inflammatory diseases for which Tocilizumab is therapeutically effective include SLE, adult onset Still disease, Takayasu arthritis, polyarteritis nodosa, systemic sclerosis, reactive arthritis, dermatomyositis, and polymyositis (Murakami et al. Current Opinion in Rheumatology 2011; 23:273-277). In addition, significant elevation of IL-6 has been found in ocular fluids derived from refractory/chronic uveitis patients, and Tocilizumab has been shown to be effective in treating uveitis (Mesquida et al. British Society for Immunology, Clinical and Experimental Immunology 2014; 176:301-309). IL-6 serum levels were also significantly increased in patients with ANCA-associated vasculitis, and treatment with Tocilizumab was able to induce a complete and sustained disease remission in a patient with severe multisystemic microscopic polyangiitis (Berti et al. Seminars in Arthritis and Rheumatism 2015; 45:48-54). Inflammatory response and quality of life measures were successfully improved by Tocilizumab of a 69-year-old man with systemic manifestations of Cogan's syndrome relapsed after prednisone induced remission for 1 year (Shibuya et al. Mod Rheumatol 2013; 23:577-581). After one year of treatment with Tocilizumab, subjects with neuromyelitis optica experienced decreased relapse rates, neuropathic pain, and general fatigue (Araki et al. Neurology 2014; 82:1302-1306). The use of Tocilizumab allowed for prednisone withdrawal at 3 months, and remission of both articular and cutaneous manifestations of eosinophilic fasciitis at 6 months (Espinoza et al. Joint Bone Spine 2015; 82:460-461). Atopic dermatitis is a multifactorial disorder associated with Th2 polarized CD4+ T cells that can overproduce IL-6. Blocking IL-6 receptor by Tocilizumab in 3 patients with severe atopic dermatitis decreased clinical activity of atopic dermatitis (Navarini et al. J Allergy Clin Immunol 2011:1128-1130).

Similarly, targeting IL-1β is also being used as a therapeutic intervention for immune disorders (Dinarello et al. Nat Rev Drug Discov. 2012; 11(8):633-652). For example, IL-1 promotes the production of IL-6, a key pathogenic factor for Castleman's disease. In the case of a 61-year-old woman with Castleman's disease refractory to treatments including cladribine, rituximab, steroids, etanercept, and anti-IL-6 monoclonal antibody, her symptoms markedly improved with recombinant IL-1 receptor antagonist (El-Osta et al. Mol Cancer Ther. 2010; 9(6):1485-1488).

The IL-6- and/or IL-1β-mediated diseases that can be treated with a composition comprising ascr #7 or a pharmaceutically acceptable salt and/or prodrug thereof include but are not limited to the diseases discussed herein.

In some embodiments, the IL-6- and/or IL-1β-mediated disease is Agammaglobulinemia, Amyloidosis, Ankylosing spondylitis, Anti-GBM/Anti-TBM nephritis, Antiphospholipid syndrome, Autoimmune hepatitis, Autoimmune inner ear disease, Atopic dermatitis, Asthma, Castleman disease, Celiac disease, Chagas disease, Chronic recurrent multifocal osteomyelitis, Cogan's syndrome, Cold agglutinin disease, CREST syndrome, Crohn's disease, Dermatomyositis, Devic's disease (neuromyelitis optica), Discoid lupus, Endometriosis, Eosinophilic esophagitis, Eosinophilic fasciitis, Evan's syndrome, Fibromyalgia, Giant cell arteritis, Giant cell myocarditis, Glomerulonephritis, Goodpasture's syndrome, Granulomatosis with polyangiitis, Graves' disease, Guillain-Barre syndrome, Hashimoto's thyroiditis, Hemolytic anemia, Henoch-Schonlein purpura, Hypogammaglobulinemia, Hypoproliferative anemia, IgA Nephropathy, Inclusion body myositis, Interstitial cystitis, Inflammatory Bowel Disease, Juvenile arthritis, Juvenile/Type 1 Diabetes, Juvenile myositis, Kawasaki syndrome, Lichen planus, Lichen sclerosus, Lupus (SLE), Meniere's disease, Multiple sclerosis, Myasthenia gravis, Microscopic polyangiitis, Optic neuritis, Pemphigus, Polyarteritis nodosa, Polymyalgia rheumatica, Polymyositis, Primary biliary cirrhosis, Primary sclerosing cholangitis, Psoriasis, Psoriatic arthritis, Rheumatic fever, Rheumatoid arthritis, Sarcoidosis, Sjogren's syndrome, Temporal arteritis/Giant cell arteritis, Transverse myelitis, Ulcerative colitis, Uveitis, Vasculitis, Vitiligo, Viral myocarditis, or Wegener's granulomatosis (Granulomatosis with Polyangiitis (GPA)).

In certain embodiments, the disease is asthma, inflammatory bowel disease, or type 1 diabetes. In certain preferred embodiments, the disease is Eosinophilic esophagitis (EoE).

The invention also provides methods of reducing IL-6 and/or IL-1β production from a cell, comprising contacting the cell with a composition comprising ascr #7 or a pharmaceutically acceptable salt or prodrug thereof. Such methods may be performed in vivo or in vitro.

IV. Subjects

The subject may be a mammal. The subject may be a rodent, lagomorph, feline, canine, porcine, ovine, bovine, equine, or primate. In some embodiments, the subject is a human. The subject may be a female or male. The subject may be an infant, child, or adult. In some embodiments, the subject has an elevated level of IL-6 and/or IL-1β.

V. Routes of Administration

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

One of skill in the art would appreciate that a method of administering a therapeutically effective substance formulation or composition of the disclosure would depend on factors such as the age, weight, and physical condition of the subject being treated, and the disease or condition being treated. The skilled worker would, thus, be able to select a method of administration optimal for a subject on a case-by-case basis.

The invention now being generally described, it will be more readily understood by reference to the following examples, which are included merely for purposes of illustration of certain aspects and embodiments of the present invention, and are not intended to limit the invention. As such, it will be readily apparent that any of the disclosed beneficial substances and therapies can be substituted within the scope of the present disclosure.

EXAMPLES

Many types of autoimmune and inflammatory diseases, have shared components of their disease mechanism. One of the main shared components involves signaling molecules, known as cytokines, which guide and direct many cellular processes. IL-6 and/or IL-1β are found to be significantly elevated in many autoimmune and/or inflammatory disorders.

The Examples variously demonstrate that ascr #7 significantly reduced levels of both IL-6 and IL-1β in an in-vitro model of inflammation. They further demonstrate that ascr #7 significantly reduces disease progression in a broad range of autoimmune and inflammatory diseases, specifically a mouse model of asthma, a mouse model of type 1 diabetes, and a mouse model of inflammatory bowel disease.

Example 1

Ascr #7 significantly reduces both IL-6 and IL-1β secretion in an in vitro model of inflammation. Specifically, ascr #7 reduces IL-6 and IL-1β in a stimulated culture of bone marrow-derived mouse dendritic cells.

a. Generation of Bone Marrow Dendritic Cells

Bone marrow was extracted from femurs of C57BL/6 mice (6-12 weeks of age). These mice were euthanized by $CO_2$ inhalation and their femurs were removed. After removing the remaining flesh from the bone, they were cut at the metaphysis. Bone marrow was flushed out using a syringe filled with RPMI. The extracted marrow was further broken down by resuspension with syringe. The mixture was centrifuged and the pellet was re-suspended in RPMI. Cells from the bone marrow were seeded in 6 wells such that each well had a density of $10^6$ cells/ml. 20 ng of GM-CSF was added to each well. At day 3, and every 3 days thereafter, the media was replaced. Cells were used for experiments between day 7-9.

b. Stimulation of Dendritic Cells: Testing the Effect of Ascr #7

Bone marrow dendritic cells were collected between day 7-9 of culture. Cells were washed twice and counted. Ascr #7 in water or RPMI were placed in corresponding wells, and are allowed to dry. $10^6$ cells were then plated in each well in a 24 well culture plate. Cells were left to incubate with ascr #7 for 5 minutes. Following the brief incubation, different TNFα was added to the wells. These bone marrow dendritic cells were then cultured at 37° C. for 18-72 hours. Cells were collected via the pellet generated by centrifuge. The supernatant was also preserved. EBioscience ELISA kits was used to determine the concentration of different cytokines present in each well. Results are shown in FIG. 1 and FIG. 2.

Figure 1:
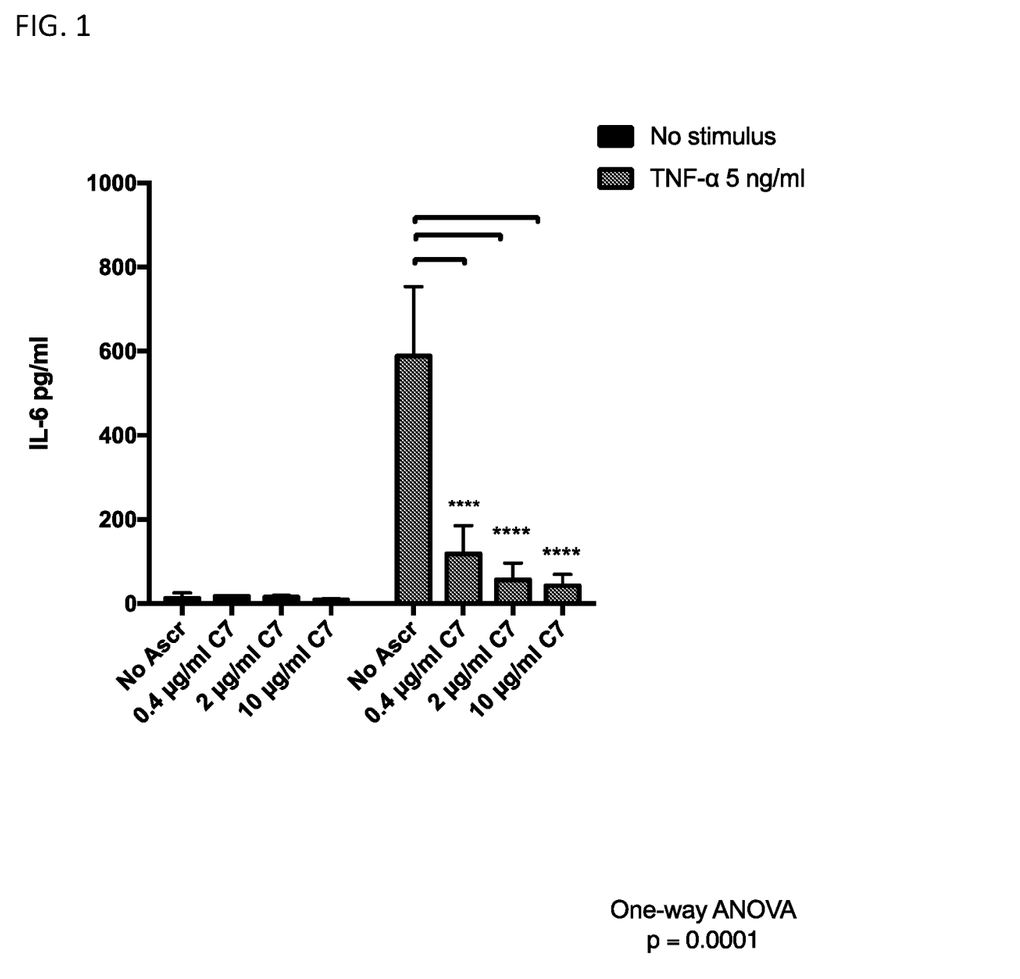
FIG. 1 shows that ascr #7 diminishes IL-6 production by testing dendritic cells in an in vitro assay.
Figure 2:
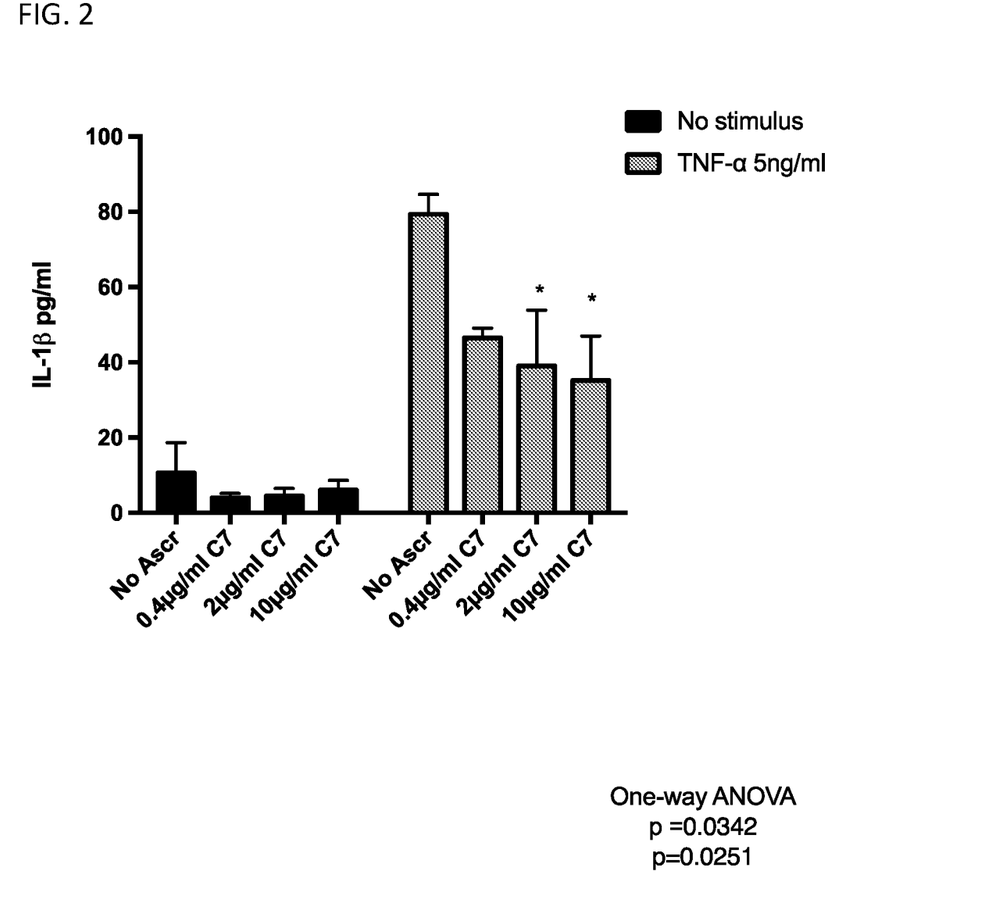
FIG. 2 shows that ascr #7 diminishes IL-1β production by testing dendritic cells in an in vitro assay.

The left side of FIG. 1 shows that the dendritic cells, when not stimulated with TNF-α, have very low levels of IL-6, and that this remains true with administration of different concentrations of ascr #7. The right side of FIG. 1 shows that dendritic cells, when stimulated with TNF-α, has very high levels of secreted IL-6 and that administration of different concentrations of ascr #7 reduces these levels significantly. The left side of FIG. 2 shows that the dendritic cells, when not stimulated with TNF-α, have very low levels of IL-1β, and that this remains true with administration of different concentrations of ascr #7. The right side of FIG. 2 shows that dendritic cells, when stimulated with TNF-α, has very high levels of secreted IL-β and that administration of different concentrations of ascr #7 reduces these levels significantly.

Example 2

Ascr #7 reduces the trademark disease pathologies in a mouse model of asthma. Specifically, ascr #7 reduces the development of eosinophilia, goblet cell metaplasia, and airway hyper-reactivity in the ovalbumin model of murine asthma.

Figure 3A:
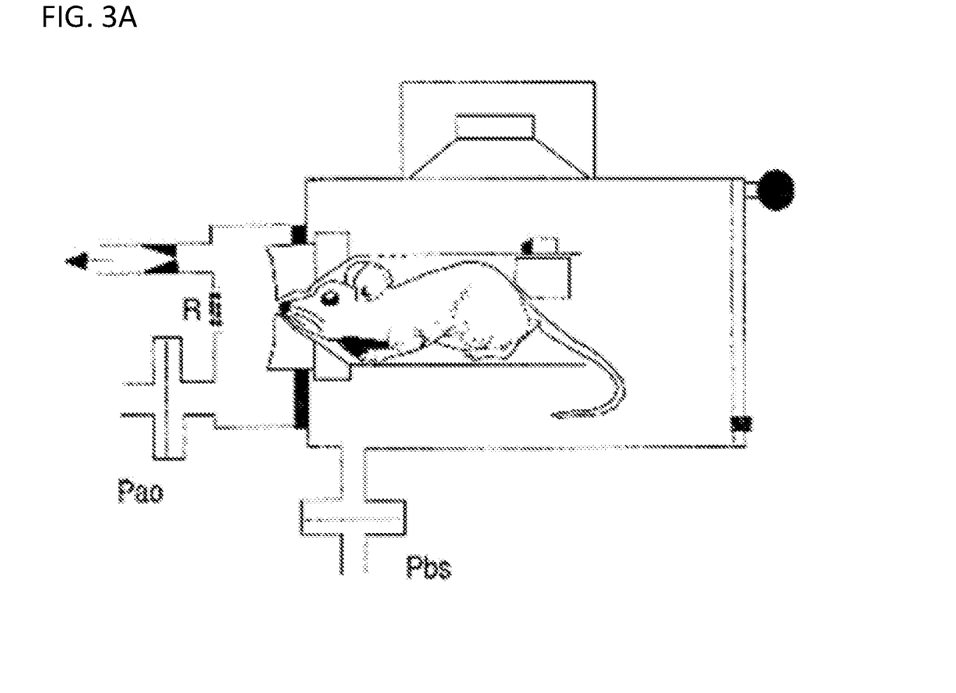
FIG. 3A shows a diagram of a mouse in a respiratory chamber.
Figure 3B:
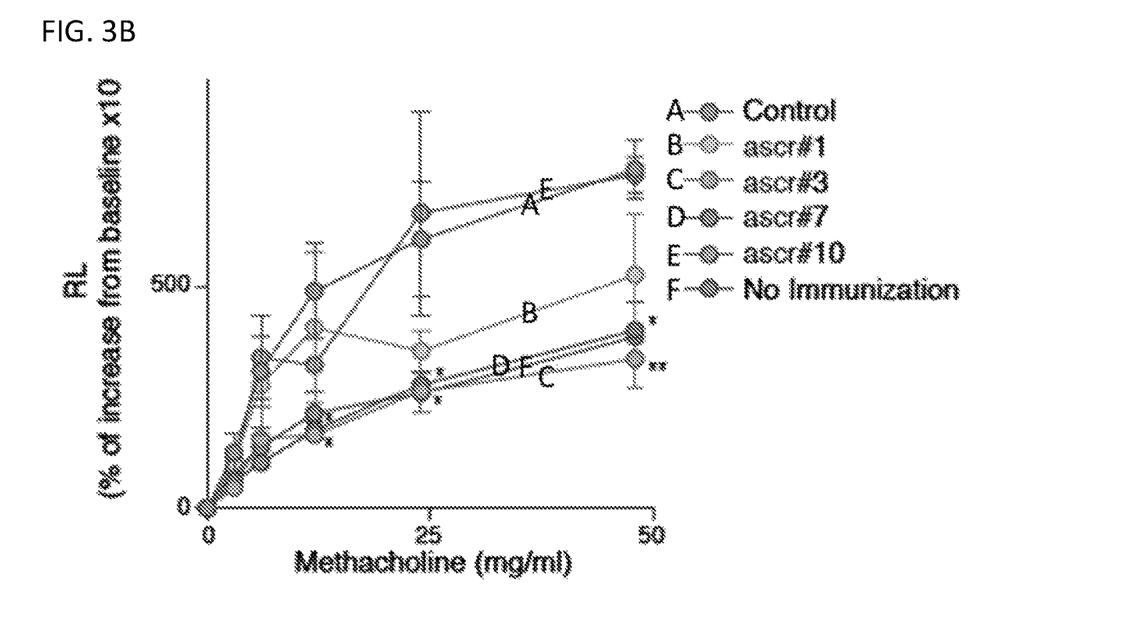
FIG. 3B shows that ascr #7 prevents hallmark pathologies of asthma.
Figure 3C:
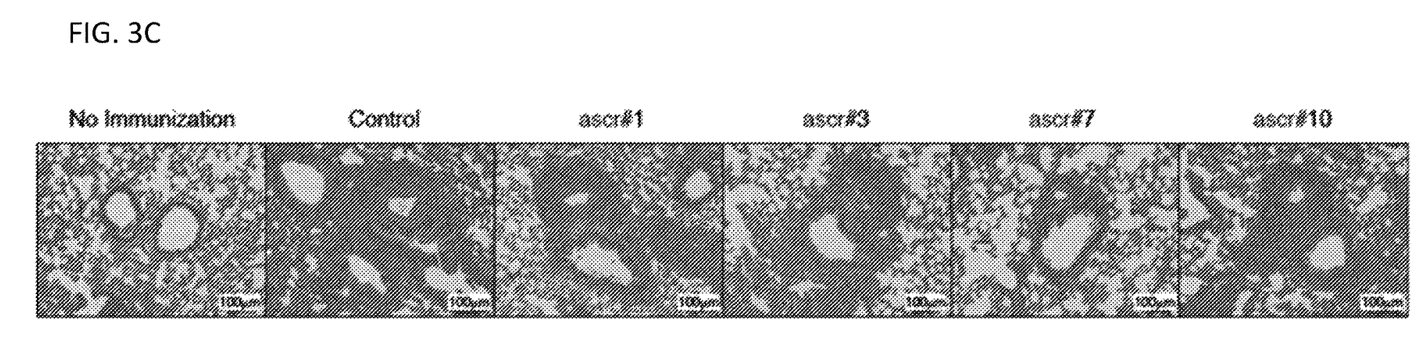
FIG. 3C shows that ascr #7 decreases the inflammatory buildup, airway restriction, and mucus secretion based on the staining of the histological sections of lungs.

Adult C57BL/6 mice were sensitized by administering 2 ug OVA (Sigma-Aldrich) and 1 mg alum (Thermo) with 50 ng ascr #7 or saline, via intraperitoneal injection, on Day 0 and 14. On day 24, the mice were challenged with intranasal administration of saline containing 100 µg OVA, under isoflurane anesthesia. Histologic sections were stained with H&E or PAS to score for eosinophilia, goblet cell metaplasia, and airway hyper-reactivity. Results are shown in FIG. 3B and FIG. 3C. Mice were also placed in a computer controlled small animal ventilator (SCIREQ) to score for airway hyper-reactivity following methacholine challenge. FIG. 3A shows a diagram of a mouse in a respiratory chamber, which has been calibrated to calculate the resistance of air flow as the animal breathes. Animals with asthma have higher resistance of flow, which would be represented as higher "RL" values in FIG. 3B. FIG. 3B shows that asthmatic mice, here labeled "Control", have higher resistance of air flow, whereas a normal mouse, here labeled "No Immunization" has low resistance of air flow. Asthmatic mice that have been administered ascr #7 demonstrate low resistance of air flow, with comparable levels to normal mice. Lungs were collected, postmortem, and then sectioned and stained to show the presence of eosinophils and mucus. These findings are shown in FIG. 3C. In FIG. 3C, the normal mouse lung, here labeled "No Immunization" shows thin boundaries between the central bronchioles and the surrounding alveoli, wherein the thin membranes allow for oxygen to easily diffuse. In FIG. 3C, the asthmatic mouse lung, here labeled "Control" has a large number of mucus and eosinophils that surround the bronchioles and occupy the alveolar space; wherein the thick barriers would prohibit oxygen from easily diffusing. In FIG. 3C, the lung of asthmatic mice that were administered ascr #7 has thin boundaries between the bronchioles and the alveolar space, comparable to the normal mice. This demonstrates that ascr #7 reduces the trademark pathologies found in asthmatic mice, specifically resistance to air flow and its associated histopathologies.

Example 3

Ascr #7 reduces the signature disease pathologies in a mouse model of Type 1 Diabetes. Specifically, ascr #7 delays conversion to hyperglycemia in a multi-genetic animal model of Type 1 Diabetes.

Figure 4A:
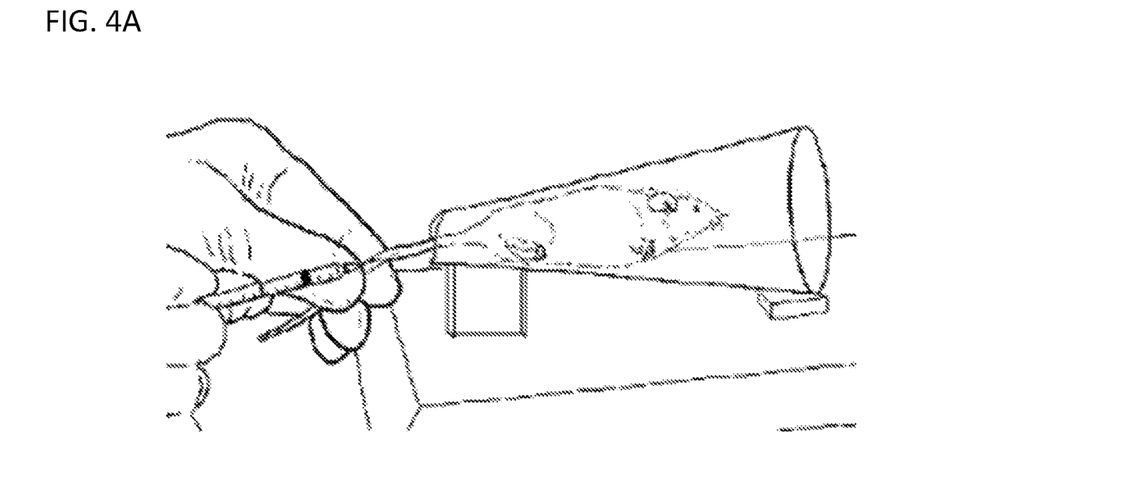
FIG. 4A shows a diagram of a mouse having a blood sample taken from the tail vein.
Figure 4B:
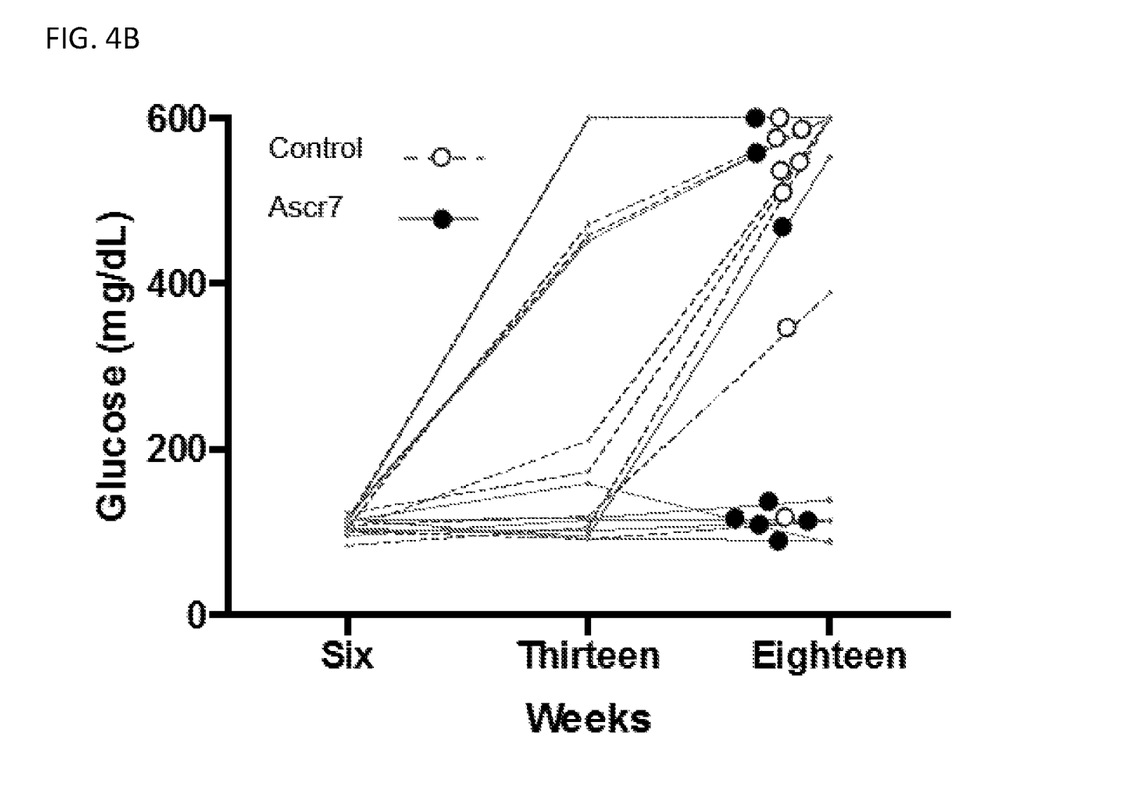
FIG. 4B shows that ascr #7 delays onset of type 1 diabetes in Non-obese diabetic (NOD) mice.

The NOD/ShiLtJ (Jackson Laboratories) mouse model of Type 1 Diabetes was used These mice typically develop hyperglycemia around 17-18 weeks of life. Either saline or 100 ng ascr #7 was administered three times a week via intraperitoneal injection. Blood glucose levels were determined in the same mouse over time, via the collected of tail vein blood (as shown in FIG. 4A) at multiple time points. FIG. 4B shows the individual blood glucose values of 16

Figure 4C:
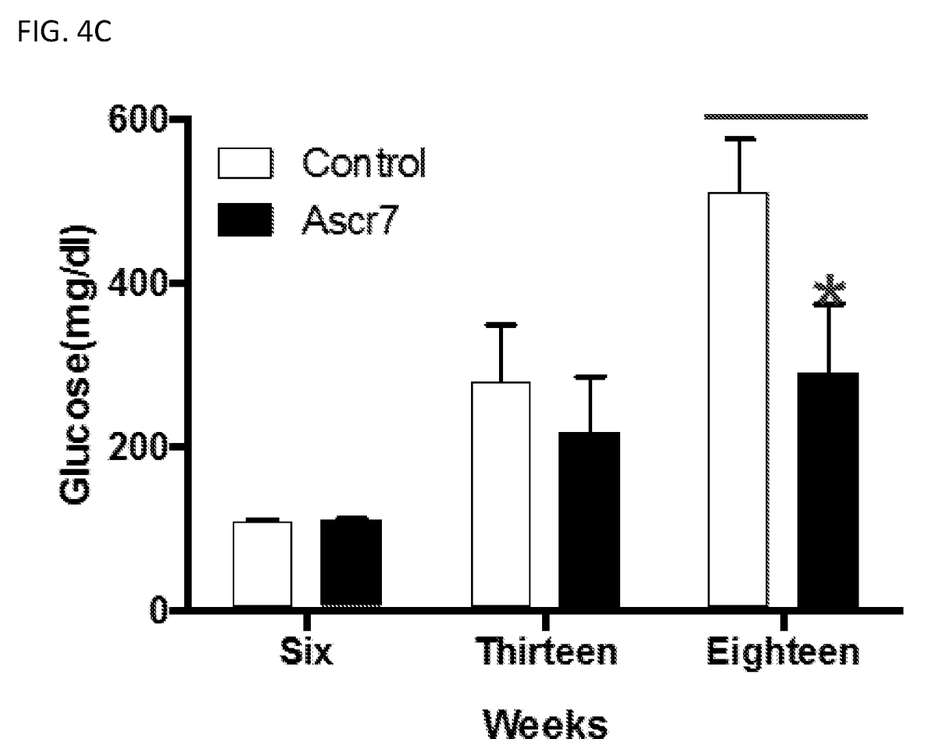
FIG. 4C shows that ascr #7 delays onset of type 1 diabetes in Non-obese diabetic (NOD) mice.

NOD/ShiLtJ mice over 18 weeks. 8 mice were injected with saline and 8 mice were injected with ascr #7, as described above. FIG. 4B demonstrates that most of the untreated mice, injected with saline (blank circles), indeed had high blood glucose values by week 18. FIG. 4B demonstrates that most of the mice treated with ascr #7 (solid circles) had significantly reduced blood glucose levels throughout 18 weeks. FIG. 4C shows the combined average and statistical error bars of the mice shown in FIG. 4B. FIG. 4C shows that at week 18, the mice treated with ascr #7 had significantly lower blood glucose levels compared to that of the untreated group.

Example 4

Ascr #7 reduces the signature disease pathologies in a mouse model of IBD. Specifically, ascr #7 markedly reduces the development of colon shortening, abnormal lumen dilation, and diarrhea in an immune dysregulation model of inflammatory bowel disease.

Figure 5:
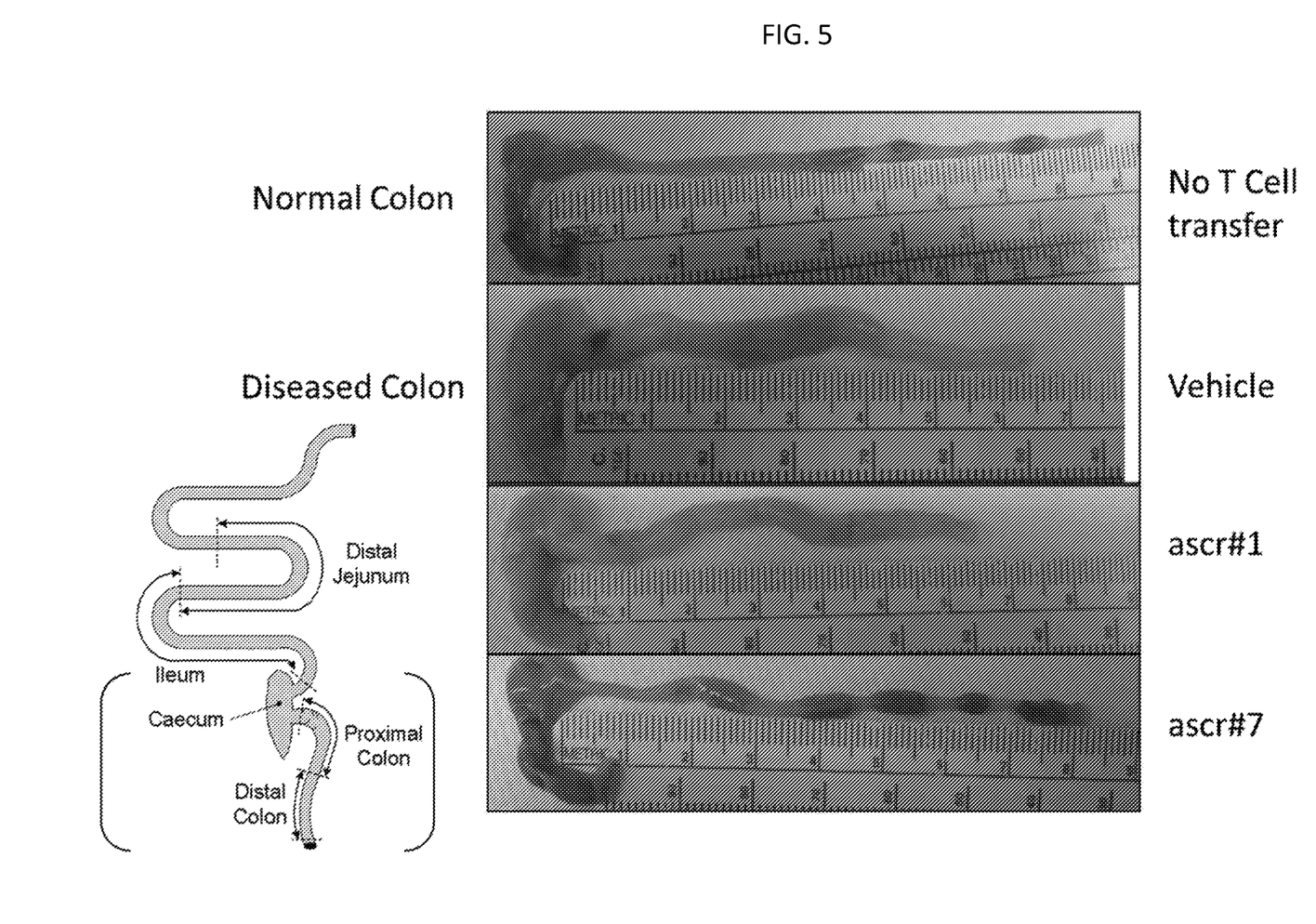
FIG. 5 shows that ascr #7 markedly reduces colon shortening and diarrhea in an immune dysregulation model of Inflammatory Bowel Disease (IBD). The inset shows a diagram of the colon.

A T cell transfer model of colitis where $10^6$CD4+ T cells were transferred to adult Rag −/− mice was used, and either saline or 300 ng ascr #7 were administered via intraperitoneal injection every 3 days between day 14 and day 28. On day 28, the mice were euthanized and colon analysis was performed. n=3 mice per group. Results are shown in FIG. 5. The inset shows a diagram of the colon. FIG. 5 shows the normal tissue architecture of a dissected caecum and colon. The normal mouse colon is long, skinny, and has discrete fecal pellets. The diseased mouse colon, with IBD, has a shortened, dilated colon, with diarrhea instead of discrete fecal pellets. The colon of a mouse with IBD, which has been administered ascr #7 has a normal appearing colon, which is long, skinny, and contains discrete fecal pellets.

INCORPORATION BY REFERENCE AND VARIATIONS

All publications and patents mentioned herein are hereby incorporated by reference in their entirety as if each individual publication or patent was specifically and individually indicated to be incorporated by reference. In case of conflict, the present specification, including its specific definitions, will control.

While specific aspects of the subject matter have been discussed, the above specification is illustrative and not restrictive. Many variations will become apparent to those skilled in the art upon review of this specification and the claims below. The full scope of the disclosure should be determined by reference to the claims, along with their full scope of equivalents, and the specification, along with such variations.

What is claimed is:

1. A method of preventing or treating an IL-6- and/or IL-1β-mediated disease in a subject, comprising administering to the subject a composition comprising ascr #7 or a pharmaceutically acceptable salt and/or prodrug thereof and a pharmaceutically acceptable carrier.

2. The method of claim 1, wherein the IL-6- and/or IL-1β-mediated disease is an autoimmune disease or an inflammatory disease.

3. The method of claim 1, wherein the subject has an elevated level of IL-6 and/or IL-1β.

4. The method of claim 1, wherein the level of IL-6 and/or IL-10 in an affected tissue of the subject exceeds 200% of a normal level in the affected tissue.

5. The method of claim 1, wherein the disease is Agammaglobulinemia, Amyloidosis, Ankylosing spondylitis, Anti-GBM/Anti-TBM nephritis, Antiphospholipid syndrome, Autoimmune hepatitis, Autoimmune inner ear disease, Atopic dermatitis, Asthma, Castleman disease, Celiac disease, Chagas disease, Chronic recurrent multifocal osteomyelitis, Cogan's syndrome, Cold agglutinin disease, CREST syndrome, Crohn's disease, Dermatomyositis, Devic's disease (neuromyelitis optica), Discoid lupus, Endometriosis, Eosinophilic esophagitis, Eosinophilic fasciitis, Evan's syndrome, Fibromyalgia, Giant cell arteritis, Giant cell myocarditis, Glomerulonephritis, Goodpasture's syndrome, Granulomatosis with polyangiitis, Graves' disease, Guillain-Barre syndrome, Hashimoto's thyroiditis, Hemolytic anemia, Henoch-Schonlein purpura, Hypogammaglobulinemia, Hypoproliferative anemia, IgA Nephropathy, Inclusion body myositis, Interstitial cystitis, Inflammatory Bowel Disease, Juvenile arthritis, Juvenile/Type 1 Diabetes, Juvenile myositis, Kawasaki syndrome, Lichen planus, Lichen sclerosus, Lupus (SLE), Meniere's disease, Multiple sclerosis, Myasthenia gravis, Microscopic polyangiitis, Optic neuritis, Pemphigus, Polyarteritis nodosa, Polymyalgia rheumatica, Polymyositis, Primary biliary cirrhosis, Primary sclerosing cholangitis, Psoriasis, Psoriatic arthritis, Rheumatic fever, Rheumatoid arthritis, Sarcoidosis, Sjogren's syndrome, Temporal arteritis/Giant cell arteritis, Transverse myelitis, Ulcerative colitis, Uveitis, Vasculitis, Vitiligo, Viral myocarditis, or Wegener's granulomatosis (Granulomatosis with Polyangiitis (GPA)).

6. The method of claim 5, wherein the disease is asthma.

7. The method of claim 5, wherein the disease is inflammatory bowel disease.

8. The method of claim 5, wherein the disease is type 1 diabetes.

9. The method of claim 5, wherein the disease is not eosinophilic esophagitis (EoE).

10. The method of claim 1, further comprising administering an agent with an anti-inflammatory effect.

11. The method of claim 10, wherein the agent with an anti-inflammatory effect is a corticosteroid.

12. The method of claim 11, wherein the corticosteroid is selected from aldosterone, betamethasone, budesonide, corticosterone, cortisol, cortisone, dexamethasone, fluticasone, hydrocortisone, methylprednisolone, prednisolone, and prednisone.

13. The method of claim 1, wherein the subject is a mammal.

14. The method of claim 13, wherein the mammal is a mouse or a human.

15. The method of claim 14, wherein the mammal is a human.

16. A method of reducing IL-6 and/or IL-1β production from a cell, comprising contacting the cell with a composition comprising ascr #7 or a pharmaceutically acceptable salt and/or prodrug thereof and a pharmaceutically acceptable carrier.

17. The method of claim 1, wherein the method is a method of treating the IL-6- and/or IL-1β-mediated disease in the subject.

18. The method of claim 1, wherein the composition comprises ascr #7 or a pharmaceutically acceptable salt thereof.

* * * * *